United States Patent [19]

Poli

[11] Patent Number: 5,396,925
[45] Date of Patent: Mar. 14, 1995

[54] ANTI-FREE FLOW VALVE, ENABLING FLUID FLOW AS A FUNCTION OF PRESSURE AND SELECTIVELY OPENED TO ENABLE FREE FLOW

[75] Inventor: Robert G. Poli, Campbell, Calif.

[73] Assignee: Abbott Laboratories, Abbott Park, Ill.

[21] Appl. No.: 168,936

[22] Filed: Dec. 16, 1993

[51] Int. Cl.[6] ............................................. F16K 17/18
[52] U.S. Cl. .................................. 137/493; 137/523; 137/845; 251/9; 251/342
[58] Field of Search ............... 251/4, 9, 342; 137/493, 137/522, 523, 845

[56] References Cited

U.S. PATENT DOCUMENTS

| | | | |
|---|---|---|---|
| 274,447 | 3/1983 | Kennish | 251/342 X |
| 2,755,060 | 7/1956 | Twyman | 251/342 |
| 3,245,428 | 4/1966 | Klimak | 137/493 |
| 3,675,891 | 7/1972 | Reynolds et al. | |
| 3,965,925 | 6/1976 | Gooch | 251/342 |
| 4,337,770 | 7/1982 | Young et al. | |
| 4,341,239 | 7/1982 | Atkinson | 137/493 |
| 4,429,852 | 2/1984 | Tersteegen | 251/9 |
| 4,434,810 | 3/1984 | Atkinson | 137/493 |

OTHER PUBLICATIONS

Vernay Duckbill Check Valves Brochure, ©1992, Vernay Laboratories, Inc. 4 pages.

Primary Examiner—Robert G. Nilson
Attorney, Agent, or Firm—Harry G. Thibault; Thomas M. Breininger

[57] ABSTRACT

A bi-directional cracking valve that can be selectively opened. Bi-directional cracking valve (10, 70) is formed using an elastomeric membrane (34). Centered within the elastomeric membrane is a slit (36) that remains closed, blocking fluid flow through the device until a differential pressure across the elastomeric membrane exceeds a predefined cracking pressure, sufficient to force fluid through the slit. The elastomeric membrane is an integral part of an elastomeric cylinder (28), which is mounted in a valve carrier (12). The valve carrier includes ports disposed at opposite ends and the ports are adapted to couple to tubing. An operator can selectively enable fluid flow through the device by squeezing side tabs (40, 42) disposed on opposite sides of the elastomeric membrane together, forcing the slit open. A latch (46) is provided to keep the bi-directional cracking valve in an open state.

15 Claims, 4 Drawing Sheets

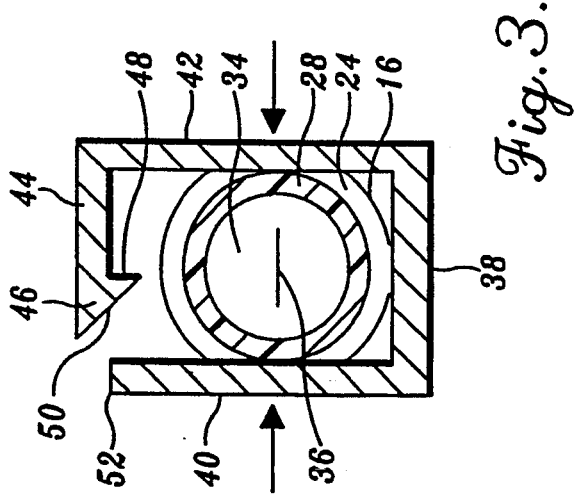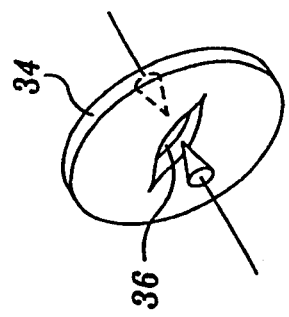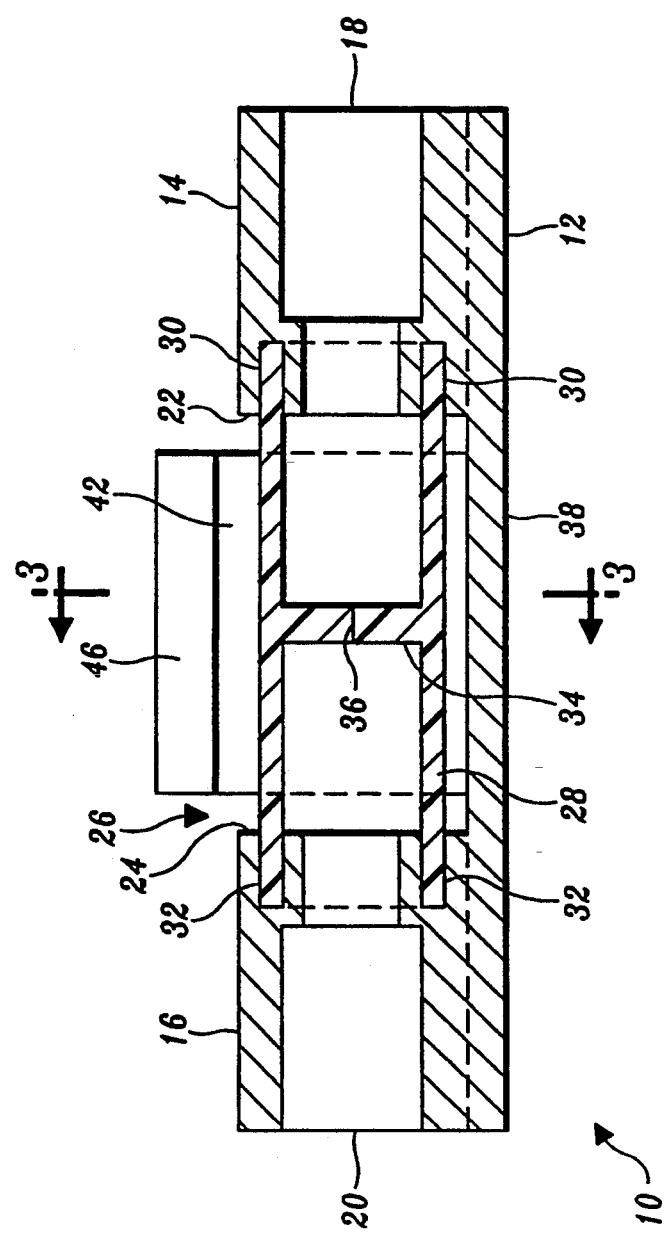

ANTI-FREE FLOW VALVE, ENABLING FLUID FLOW AS A FUNCTION OF PRESSURE AND SELECTIVELY OPENED TO ENABLE FREE FLOW

FIELD OF THE INVENTION

The present invention generally pertains to a flush valve, and more specifically, to a valve that normally limits a flow of fluid through the valve until it is selectively opened by deforming an elastomeric portion of the valve to enable a much greater rate of fluid flow.

BACKGROUND OF THE INVENTION

There are a number of specific applications for a valve designed to block fluid flow until a pressure differential across the valve exceeds a predefined pressure, causing the valve to open. Such valves are referred to as "cracking valves" because they "crack open" when the fluid pressure exceeds the cracking pressure. An example of such a valve is disclosed in commonly assigned U.S. Pat. No. 5,055,001, which also discloses a volumetric pump in which cracking valves are employed. In this patent, a spring biased foot applies a force on a section of tubing that collapses the tubing to prevent fluid from flowing through it until the fluid pressure inside the tubing exceeds the cracking pressure of the spring, forcing open the collapsed tubing sufficiently to allow fluid to flow through it. This type of cracking valve is mechanically relatively complex and relatively expensive to fabricate.

The cracking valve discussed above can be fully opened to allow free fluid flow through the section of tubing simply by lifting the spring biased foot away from the section of tubing so that the tubing assumes its normal round cross-section due to its inherent elastic properties. The volumetric pump drive mechanism described in the patent uses a motor actuated cam to open an inlet cracking valve to allow fluid to fill pumping portion of the tubing. However, the design for a cracking valve disclosed in this patent is not practical for use in other applications in which free flow of fluid through a line must be prevented.

For example, when a tube set used in connection with a pump to deliver drugs intravascularly to a patient is being installed in the pump, free fluid flow through the tubing from the source must be prevented until the tubing is installed in the pump. Normally, once the tube set is latched into the pump, some mechanism in the pump compresses the tubing to prevent free flow of the fluid. The most common solution to this problem is simply to apply a pinch clamp to the tube set until it is installed in the pump. While this approach works, the pinch clamp is just another piece of equipment to assemble when setting up the drug infusion system. In addition, the operator sometimes forgets to remove the pinch clamp, which prevents the infusion from proceeding, or at least delays the infusion, since most pumps include sensors to detect the lack of fluid flow through the tube set and initiate an alarm.

Before a tube set is coupled to a catheter implaced in the patient's vascular system and installed in the pump, it is typically filled with the infusate by briefly allowing free flow of the fluid through the line. The pinch clamp is then applied so that the primed tube set can be installed in the pump. Clearly, it would be more convenient to use a single valve disposed downstream of the pump that can be manually opened to allow free flow of fluid to initially prime a tube set. This valve should also block fluid flow through the tubing unless the pressure is greater than a predefined cracking pressure. By selecting a cracking pressure substantially less than that produced by the pump, fluid flow through the valve would be enabled once the pump is started.

Valves that enable fluid flow when squeezed are known in the art. For example, U.S. Pat. No. 4,337,770 discloses a flow regulating device for arterial catheter systems in which the device normally provides a continuous, regulated flow of a medical fluid to a catheter, but when squeezed, provides a substantially larger flow of fluid. The device includes a control member having an inlet adapted to be connected by tubing to a source of medical fluid and an outlet adapted to be connected by tubing to a catheter. A flexible conduit defines a portion of a first passage between the inlet and outlet. A cylindrical, hollow extension extends from the outlet, coaxially within the flexible conduit, to about its midsection. A cylindrical plug member is also positioned coaxially within the flexible conduit and has a raised band intermediate its ends, of sufficient diameter to seal peripherally against the inside of the flexible conduit when the flexible conduit is not being squeezed. A capillary bore extends through the plug member, along its central longitudinal axis, enabling fluid to flow through the device at the relatively slow, continuously regulated rate. However, when the flexible conduit is squeezed, the seal between the raised band on the plug member and the interior surface of the flexible conduit is broken, and fluid flows in a substantially greater volume around the plug member, through passages created by distortion of the flexible conduit. This device thus uses the elastomeric properties of the flexible conduit to selectively enable a controlled increased flow of fluid. The valve defined by the plug member and the flexible conduit thus represents a relative simple configuration that is low cost and easy to manufacture. However, the restricted flow of fluid through the capillary bore provided when the flexible conduit is not squeezed is unacceptable for applications requiring fluid to flow freely through the valve if the fluid pressure exceeds a cracking pressure.

A cracking valve, which like the flow regulating device just discussed, opens to allow full flow when squeezed would provide substantial benefits over prior art devices for controlling fluid flow. When desired, a fluid flow sufficient to prime a catheter system could readily be implemented by simply squeezing the cracking valve. However, free fluid flow through the valve would be blocked until fluid pressure produced by a pump coupled to the line exceeded the cracking pressure.

SUMMARY OF THE INVENTION

In accordance with the present invention, a valve that limits free fluid flow until selectively opened by squeezing it, comprises a valve body having a first port and a second port. Disposed within the valve body, intermediate the first and second ports is a generally planar elastomeric membrane having opposed surfaces. A slit is disposed within the elastomeric membrane, extending between its opposed surfaces. Fluid flow between the first and the second ports is enabled when the slit opens in response to a fluid pressure across the elastomeric membrane exceeding a cracking pressure. Also included are means for selectively deforming the elastomeric membrane to force the slit to spread apart, forming a substantially unrestricted path through the valve, so that when thus selectively opened, fluid flows freely between the first and second ports.

The elastomeric membrane is secured and supported around its periphery by the valve body. Preferably, the valve body comprises an elastomeric material, and the means for selectively deforming comprise tabs that extend externally of the valve body, on opposite sides of it. The tabs distort the valve body when squeezed by an operator, so that the distorted valve body deforms the elastomeric membrane to spread apart the slit.

The means for selectively deforming also preferably include means for selectively latching the elastomeric membrane in a deformed state in which the slit has been forced to spread apart, allowing fluid to continuously flow freely through the valve. In this case, the means for selectively latching the elastomeric membrane include a latch that extends from one tab to engage the other tab when the tabs are squeezed together.

Alternatively, the means for selectively deforming can comprise at least one tab that acts on the elastomeric membrane so as to deform the elastomeric membrane when the tab is moved by squeezing it.

The valve preferably includes a carrier that supports the valve body, and the means for selectively deforming then comprise pliable portions of the carrier. When squeezed together, these pliable portions pinch the valve body, causing deformation of the elastomeric membrane to form the substantially unrestricted path through the valve. In this embodiment, the carrier is attached to opposite ends of the valve body and coupled to the first and second ports.

It is also preferred that the elastomeric membrane and the valve body comprise an integrally formed silastic material. The valve body is generally elongate in shape and the elastomeric membrane extends transversely across a longitudinal axis of the valve body.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 is a longitudinal side cross-sectional view of the valve shown in FIG. 1;

FIG. 3 is a cross-sectional view of the valve, taken along sections lines 3—3 in FIG. 2;

FIG. 4 is an isometric cutaway view of a planar elastomeric membrane of the valve in which a slit is formed, showing the slit spread apart when force is applied to diagramatically opposite edges of the membrane;

DETAILED DESCRIPTION OF THE PREFERRED EMBODIMENT

Figure 1:
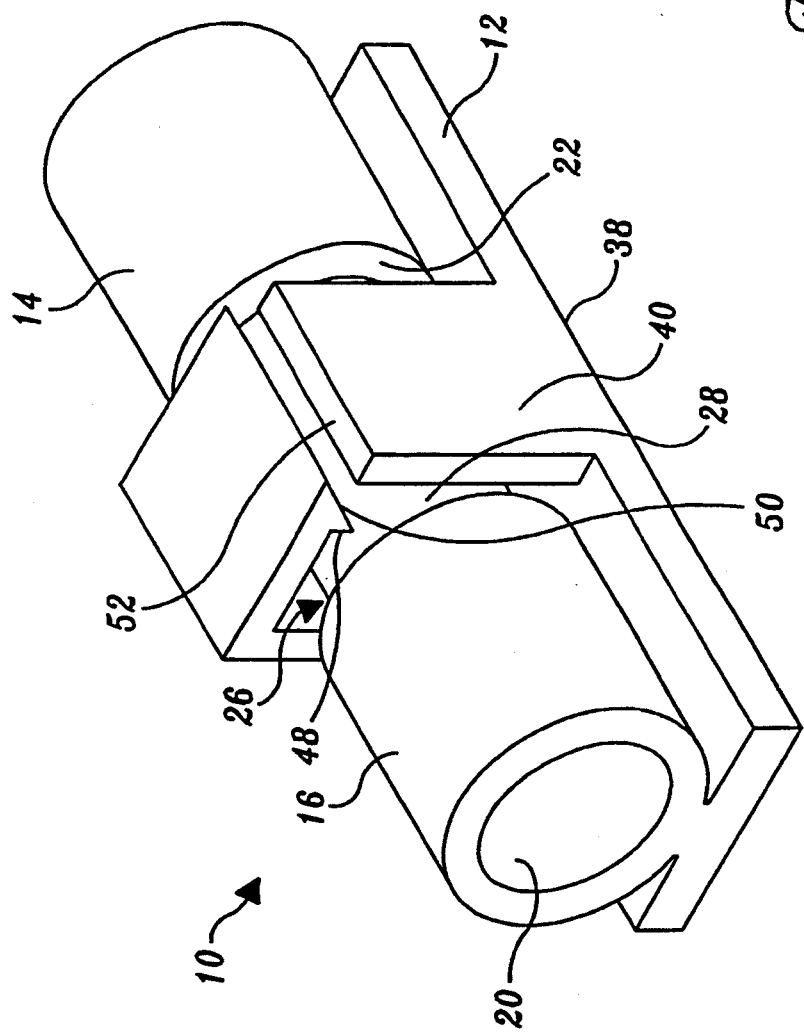
FIG. 1 is an isometric view of a valve configured in accordance with the present invention.

Referring to FIGS. 1-3, a bi-directional cracking valve 10 in accordance with the present invention is illustrated in several different views. Details of bi-directional cracking valve 10 are perhaps most evident in a cross-sectional view shown in FIGS. 2 and 3. A valve carrier 12 of the bi-directional cracking valve includes a first tubing coupler 14 at one end, and at the opposite end, a second tubing coupler 16. First and second tubing couplers 14 and 16 are generally cylindrical in shape, having a longitudinal axis which extends through the center of a first port 18 and a second port 20, respectively. First and second ports 18 and 20 are adapted to connect with the ends of tubing (not shown), which are inserted therein and bonded in place using an appropriate adhesive or solvent, or held in place by a friction fit.

First and second tubing couplers 14 and 16 have respective opposed inner ends 22 and 24, between which is defined a gap 26. In the preferred embodiment of bi-directional cracking valve 10, gap 26 extends over slightly more than one-third the total length of the valve carrier. On the facing surfaces of inner ends 22 and 24 are formed annular grooves 30 and 32, respectively, generally centered about the longitudinal axis extending through the first and second ports. Mounted in annular grooves 30 and 32 are the ends of an elastomeric cylinder 28. An appropriate adhesive or solvent is used to bond elastomeric cylinder 28 within annular grooves 30 and 32 during fabrication of bi-directional cracking valve 10, or the elastomeric cylinder is held within annular grooves 30 and 32 by a friction fit.

Centered transversely within elastomeric cylinder 28, at about its mid point, is an integrally formed elastomeric membrane 34, which extends diametrically across and between the inner circumferential surfaces of the elastomeric cylinder. A slit 36 extends through elastomeric membrane 34, diametrically across the elastomeric membrane's surface. The elastomeric membrane and elastomeric cylinder preferably comprise a silastic material.

Elastomeric membrane 34 blocks fluid flow through bi-directional cracking valve 10, between first port 18 and second port 20, until a differential fluid pressure across the elastomeric membrane exceeds a predefined cracking pressure. The magnitude of the predefined cracking pressure is established during the design of the bi-directional cracking valve, by specifying certain characteristics of the elastomeric membrane, such as its thickness, elasticity, and surface area. By controlling these parameters, it is possible to establish a relatively low cracking pressure, e.g., only a few inches of water column. If the differential pressure in either direction across elastomeric membrane 34 is less than the predefined cracking pressure, fluid does not normally flow through bi-directional cracking valve 10. However, once this cracking pressure is exceeded, slit 36 is forced open, allowing fluid to flow from which ever of the first and second ports 18 and 20 that is at a higher pressure, to the other.

Alternatively, slit 36 can be selectively manually opened to enable a substantial flow of fluid between first port 18 and second port 20, by squeezing on diametrically opposite sides of elastomeric membrane 34. The opposed force applied to opposite sides of the elastomeric membrane spreads apart slit 36, enabling fluid to flow through the open slit, between the first and second ports.

To facilitate manual opening of bi-directional cracking valve 10 in this manner, the device is provided with a side tab 40 and a side tab 42, both of which extend upwardly from a bridge 38 that connects first tubing coupler 14 to second tubing coupler 16 and extends between the two along the bottom of valve carrier 12. Normally, side tabs 40 and 42, which are disposed within gap 26, extend upwardly from bridge 38, in tangential contact with elastomeric cylinder 28 and on opposite sides of it. Furthermore, slit 36 is oriented generally transverse to side tabs 40 and 42. Thus, opposite ends of slit 36 are disposed generally adjacent to side tab 40 and 42, respectively.

An operator can selectively force slit 36 to spread apart to enable fluid flow through bi-directional cracking valve 10 by squeezing side tab 40 toward tab 42, for example, by grasping the two tabs between thumb and fore finger and applying a squeezing force. This force is coupled into the elastomeric membrane, generally as shown in FIG. 4, enabling fluid to flow through the bi-directional cracking valve.

To lock the bi-directional cracking valve in an open state, side tab 42 includes an arm 44 that extends part way across the top of the device, generally parallel to bridge 38, as seen best in FIG. 3. Arm 44 includes a latch 46 on its distal end, disposed opposite the upper end of side tab 40 (as shown in the figure). Latch 46 includes a downwardly extending engagement surface 48. A sloping surface 50 is disposed at the distal end of arm 44, extending at an acute angle relative to the top of the arm and angled back toward engagement surface 48; the angle of this sloping surface enables latch 46 to slide over a top edge 52 of side tab 40, when side tabs 40 and 42 are squeezed together by an operator. When sufficient pressure is applied to the outer surfaces of side tabs 40 and 42 so that engagement surface 48 latches onto the outer surface of side tab 40, the operator can then release the force applied to squeeze side tabs 40 and 42 toward each other, since the tabs are latched in a deflected position so as to maintain slit 36 open.

To allow slit 36 to close after bi-directional cracking valve 10 has been latched into an open condition, the operator simply lifts sloping surface 50, releasing engagement surface 48 clear of top edge 52. The inherent elasticity of side tabs 40 and 42 cause them to return to their normal position, as shown generally in FIG. 3. Slit 36 then closes, blocking fluid flow through the bi-directional cracking valve, unless the differential fluid pressure across elastomeric membrane 34 exceeds the cracking pressure.

Figure 5:
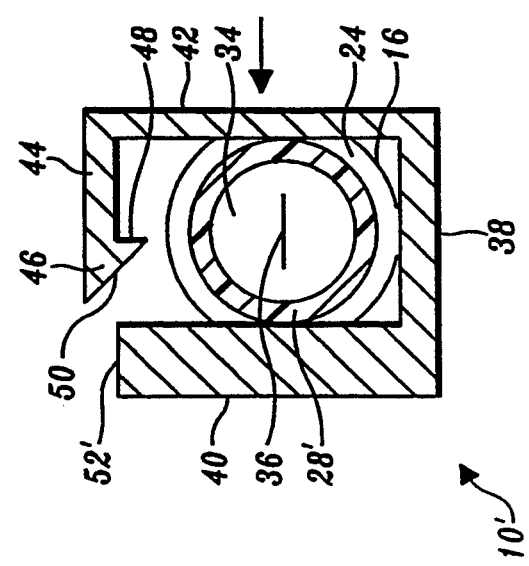
FIG. 5 is a transverse sectional view of a second embodiment of the bi-directional cracking valve.

Various modifications to bi-directional cracking valve 10 will be apparent to those of ordinary skill in the art. For example, as shown in FIG. 5, a bi-directional cracking valve 10' has a relatively thicker side tab 40' than side tab 40 in bi-directional cracking valve 10. Side tab 40' is thus much stiffer than side tab 42 and remains substantially undeflected when side tabs 40' and 42 are squeezed together. Due to this difference in stiffness, only side tab 42 deflects sufficiently to compress elastomeric cylinder 28. The compression forces slit 36 open, enabling fluid flow through the device.

Figure 6:
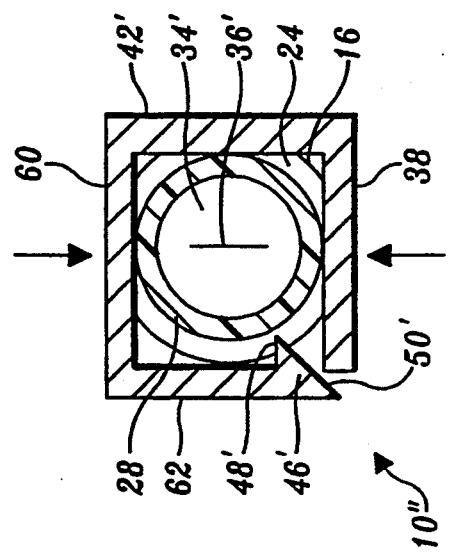
FIG. 6 is a transverse sectional view of a third embodiment of the bi-directional cracking valve.

It is also contemplated that the configuration of the tabs and the orientation of slit 36 can be changed to form a bi-directional cracking valve 10'', which is shown in FIG. 6. In this embodiment, a side tab 42' is used in place of side tab 42. Side tab 42' is shorter than side tab 42 and is coupled at a right angle to an arm 60 disposed in tangential contact above elastomeric cylinder 28. A downwardly depending arm 62 is connected to arm 60. Downwardly depending arm 62 has a latch 46' like latch 46 on arm 44 in bi-directional cracking valve 10, i.e., latch 46' includes a sloping surface 50' that is angled back to an engagement surface 48'. To keep bi-directional cracking valve 10'' in an open state, arm 60 is squeezed toward bridge 38 to engage latch 46' with the under surface of bridge 38.

Figure 7B:
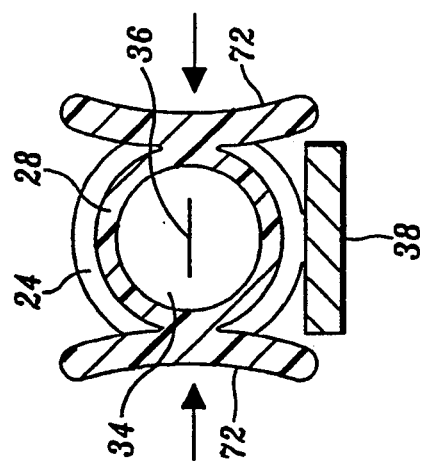
FIG. 7B is a transverse sectional view of the fourth embodiment of the bi-directional cracking valve.
Figure 7A:
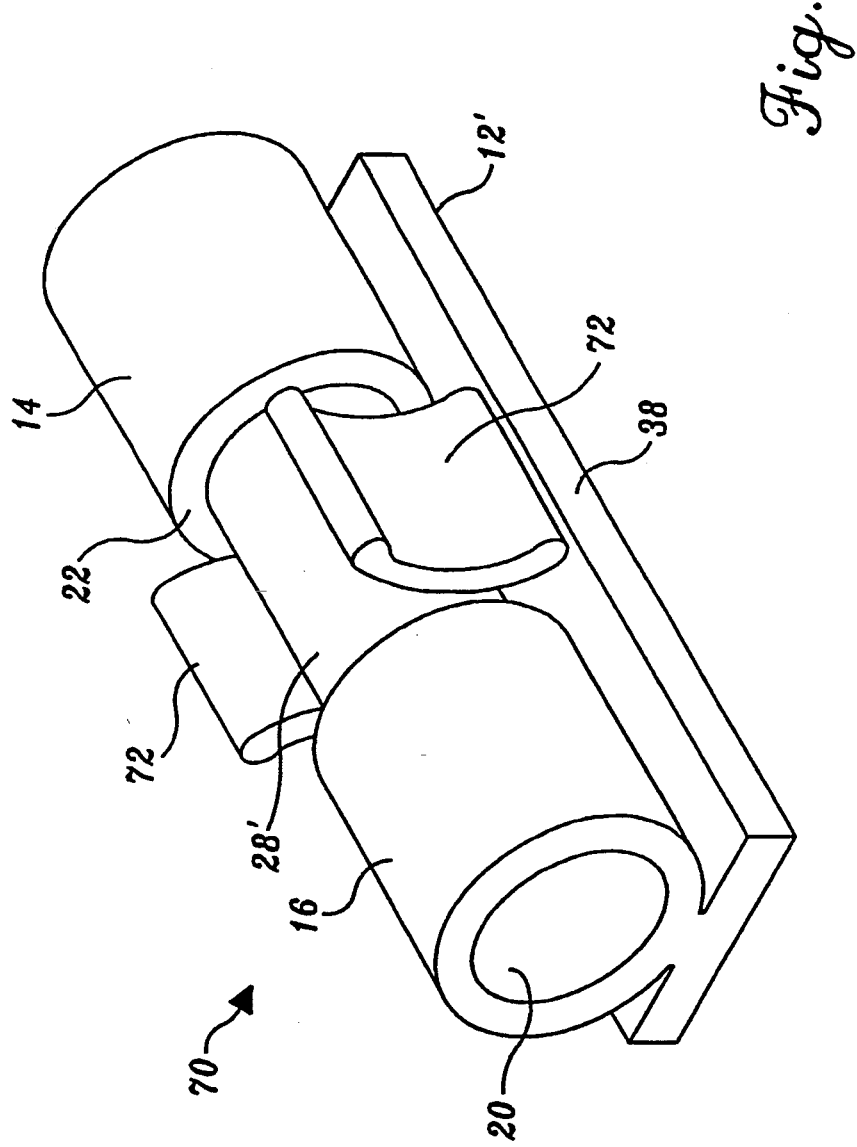
FIG. 7A is an isometric view of a fourth embodiment of the bi-directional cracking valve.

Another embodiment of a bi-directional cracking valve 70 is shown in FIGS. 7A and 7B. In this embodiment, the tabs on the valve carrier are eliminated and are instead integrally formed as part of an elastomeric cylinder 28', so that they define finger pads 72 against which the compression force is exerted by the thumb and forefinger of an operator to selectively open slit 36. There is no latching mechanism in bi-directional cracking valve 70, but it will be apparent that parallel longitudinally extending ratchets could be provided on bridge 38 to engage the lower edges of finger pads 72 when the finger pads are compressed toward each other, thereby locking the bi-directional valve in an open state.

Although the preferred embodiments of the bi-directional cracking valve have each employed a valve carrier, it will be apparent that the elastomeric cylinder and elastomeric membrane can be used without the valve carrier by coupling tubing directly to the ends of the elastomeric cylinder, using an appropriate solvent or adhesive bond or by friction fit. By squeezing on opposite sides of the elastomeric cylinder, the slit in the elastomeric membrane would be forced open to selectively allow fluid flow through the bi-directional cracking valve. This embodiment is not expressly shown; however, its configuration should be evident from the drawings, since no additional parts are needed. Instead the valve carrier is simply deleted.

These and other modifications of the bi-directional cracking valve will be apparent to those of ordinary skill in the art within the scope of the claims that follow. Accordingly, it is not intended that the scope of the invention in anyway be limited by the disclosure, but instead that it be determined entirely by reference to the claims.

The embodiments of the invention in which an exclusive property or privilege is claimed are defined as follows:

1. A valve that limits free fluid flow until selectively opened, comprising:
   (a) a valve body of elastomeric material having a first port and a second port;
   (b) a generally planar elastomeric membrane having opposed surfaces, said elastomeric membrane being disposed within the valve body, intermediate the first and second ports, secured and supported around its periphery by the valve body;
   (c) a slit disposed within said elastomeric membrane, extending between its opposed surfaces, fluid flow between the first and the second ports being enabled when the slit opens in response to a fluid pressure across the elastomeric membrane exceeding a cracking pressure;
   (d) tabs that extend externally of the valve body, on opposite sides thereof, said tabs distorting the valve body when squeezed by an operator, so that the distorted valve body deforms the elastomeric membrane to force the slit to spread apart, forming a substantially unrestricted path of fluid communication through the valve, so that fluid freely flows between the first and second ports; and (e) the tabs for selectively deforming including means for selectively latching the elastomeric membrane in a deformed state in which the slit has been forced to spread apart, allowing fluid to continuously flow freely through the valve.

2. The valve of claim 1, wherein the means for selectively latching the elastomeric membrane comprise a latch that extends from one tab to engage the other tab when the tabs are squeezed together.

3. The valve of claim 1, wherein at least one tab is coupled to the elastomeric membrane so as to deform the elastomeric membrane when the tab is moved by squeezing it.

4. The valve of claim 1, wherein the elastomeric membrane and the valve body comprise an integrally formed silastic material.

5. The valve of claim $, wherein the valve body is generally elongate in shape and the elastomeric membrane extends transversely across a longitudinal axis of the valve body.

6. A valve that blocks fluid flow as a function of fluid pressure, but which can be selectively opened, comprising:

(a) a transverse barrier formed within a valve body, said valve body having first and second ports between which the transverse barrier is disposed;

(b) a slit formed in the transverse barrier, said slit being forced open to enable a fluid flow through the valve body between the first and second ports in response to a differential fluid pressure acting on the transverse barrier in excess of a cracking pressure, said cracking pressure being sufficient to enable fluid to flow through the slit;

(c) a carrier for the valve body, said carrier supporting the valve body and including opposed flexible members disposed on opposite sides of the valve body, said flexible members being adapted to distort the valve body when squeezed toward each other, causing the slit in the transverse barrier to spread apart and enabling substantially free fluid flow through the valve body.

7. The valve of claim 6, wherein the carrier is coupled to opposite ends of the valve body, extending around the first and second ports so that a fluid path through the valve body also passes through the carrier.

8. The valve of claim 7, wherein the carrier includes a base that extends adjacent to the valve member, said base supporting the flexible members so that they extend transversely to the base, adjacent the opposite sides of the valve member.

9. The valve of claim 6, wherein the transverse barrier and the valve body are integrally formed.

10. The valve of claim 6, wherein the slit extends generally in a direction that is transverse to the flexible members, so that the valve body is compressed between the flexible members and its distortion is coupled to the transverse barrier to force open the slit.

11. The valve of claim 6, further comprising a latch that is attached to one of the flexible members and selectively engages the other flexible member when the two flexible members are squeezed together, said latch maintaining the valve body in a distorted state, thereby keeping the slit spread apart to provide a substantially continuous free fluid flow through the valve.

12. The valve of claim 6, wherein one of the flexible members is substantially more rigid than the other, said other flexible member being adapted to compress the valve body against said one flexible member when squeezed toward said one flexible member, so as to spread apart the slit to provide the substantially free flow through the valve.

13. The valve of claim 6, wherein the valve body is substantially cylindrical in shape, the first and second ports being defined by opposite open ends of the valve body.

14. A valve that limits free fluid flow until selectively opened, comprising:

(a) a valve body having a first port and a second port;

(b) a generally planar elastomeric membrane having opposed surfaces, said elastomeric membrane being disposed within the valve body, intermediate the first and second ports;

(c) a slit disposed within said elastomeric membrane, extending between its opposed surfaces, fluid flow between the first and the second ports being enabled when the slit opens in response to a fluid pressure across the elastomeric membrane exceeding a cracking pressure;

(d) means for selectively deforming the elastomeric membrane to force the slit to spread apart, forming a substantially unrestricted path of fluid communication through the valve, so that fluid freely flows between the first and second ports; and (e) a carrier that supports the valve body, said means for selectively deforming comprising pliable portions of the carrier that when squeezed together, pinch the valve body, causing deformation of the elastomeric membrane to form the substantially unrestricted path through the valve.

15. The valve of claim 14, wherein the carrier is attached to opposite ends of the valve body, coupled to the first and second ports.

* * * * *